United States Patent
Abe et al.

(10) Patent No.: US 10,006,894 B2
(45) Date of Patent: Jun. 26, 2018

(54) FLOW MEASURING DEVICE AND FLOW MEASURING SYSTEM

(71) Applicant: Daifuku Co., Ltd., Osaka-shi (JP)

(72) Inventors: Takeshi Abe, Hinocho (JP); Tadahiro Yoshimoto, Hinocho (JP)

(73) Assignee: Daifuku Co., Ltd., Osaka-shi (JP)

( * ) Notice: Subject to any disclaimer, the term of this patent is extended or adjusted under 35 U.S.C. 154(b) by 0 days. days.

(21) Appl. No.: 15/699,018

(22) Filed: Sep. 8, 2017

(65) Prior Publication Data

US 2018/0074031 A1 Mar. 15, 2018

(30) Foreign Application Priority Data

Sep. 9, 2016 (JP) ................................ 2016-176978

(51) Int. Cl.
*G01F 1/28* (2006.01)
*G01N 33/00* (2006.01)
*H01L 21/67* (2006.01)
*H01L 21/673* (2006.01)
*H01L 21/677* (2006.01)

(52) U.S. Cl.
CPC .......... *G01N 33/0009* (2013.01); *G01F 1/28* (2013.01); *H01L 21/67253* (2013.01); *H01L 21/67393* (2013.01); *H01L 21/67769* (2013.01)

(58) Field of Classification Search
CPC ..................................... G01F 1/28; G01F 1/56
See application file for complete search history.

(56) References Cited

U.S. PATENT DOCUMENTS

| 9,257,320 | B2 * | 2/2016 | Fosnight | H01L 21/67775 |
| 9,541,534 | B2 | 1/2017 | Otsuka et al. | |
| 2004/0191032 | A1 * | 9/2004 | Foulke | B65G 1/04 414/280 |
| 2008/0156069 | A1 * | 7/2008 | Murata | G01D 21/00 73/19.04 |
| 2015/0369643 | A1 * | 12/2015 | Murata | G01F 1/56 73/861.08 |

FOREIGN PATENT DOCUMENTS

JP 201512040 A 1/2015

* cited by examiner

*Primary Examiner* — Jewel V Dowtin
(74) *Attorney, Agent, or Firm* — The Webb Law Firm

(57) ABSTRACT

A flow measuring device includes an intake portion configured to be connected to an ejecting portion, one or more gas lines each of which is connected to the intake portion and in which gas ejected from the ejecting portion flows, one or more flow meters each of which is configured to measure a flow rate of gas that flows through corresponding one of the one or more gas lines, at least one resisting member configured to provide resistance to flow of gas in at least one of the one or more gas lines, a main body portion which includes one or more supported portions each configured to be supported by the support member, the main body portion being configured to support the intake portion, the one or more gas lines, the one or more flow meters, and the at least one resisting member. The magnitude of the resistance provided by the at least one resisting member is adjustable.

4 Claims, 8 Drawing Sheets

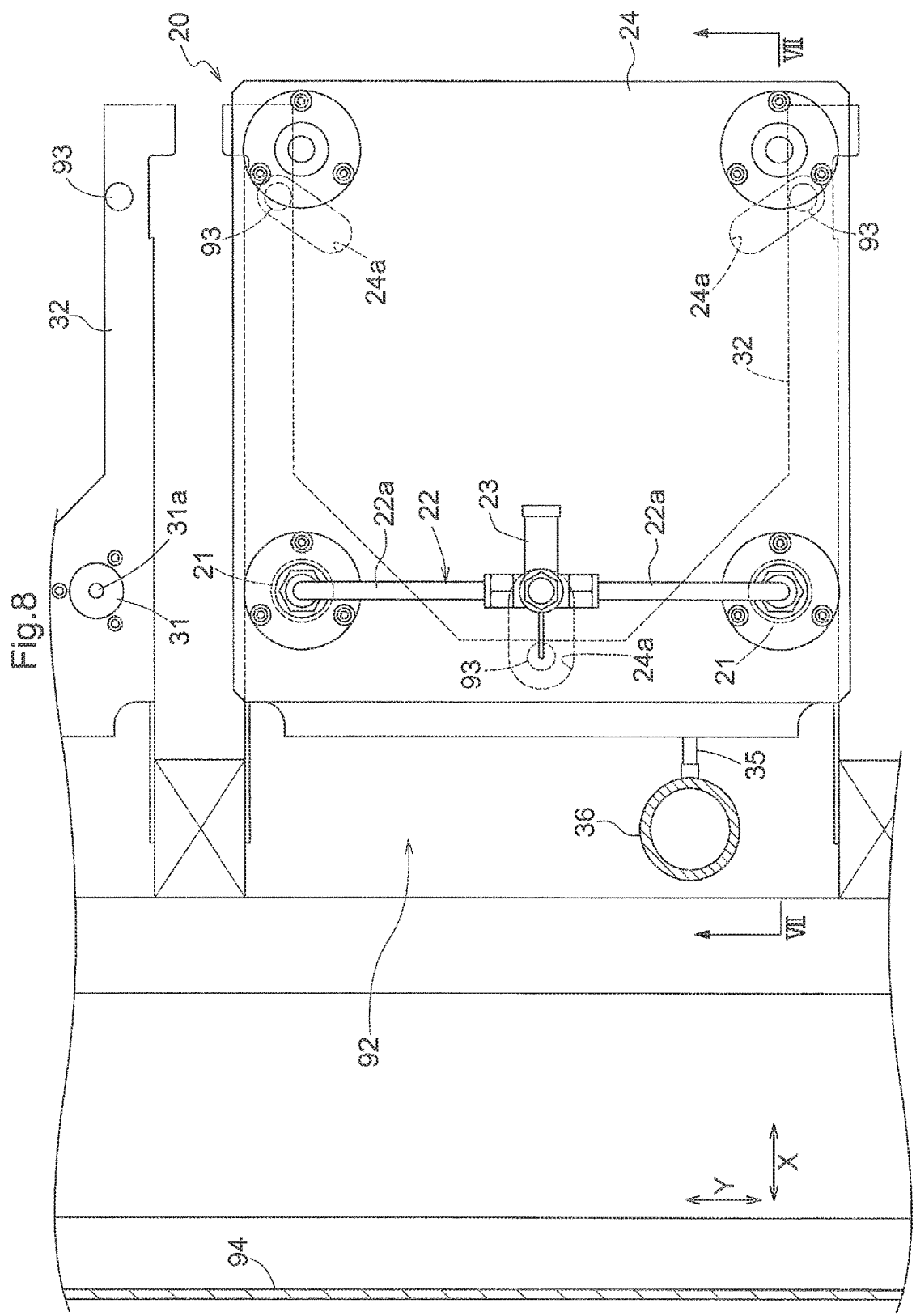

FLOW MEASURING DEVICE AND FLOW MEASURING SYSTEM

CROSS-REFERENCE TO RELATED APPLICATION

This application claims priority to Japanese Patent Application No. 2016-176978 filed Sep. 9, 2016, the disclosure of which is hereby incorporated in its entirety by reference.

FIELD OF THE INVENTION

The present invention relates to a flow measuring device and a flow measuring system which are used to inspect a clean gas supplying device.

BACKGROUND

A known inspecting device that functions as a flow measuring device used to inspect a clean gas supplying device is described in JP Publication of Application No. 2015-12040 (Patent Document 1). More specifically, Patent Document 1 discloses an inspecting device (1) for inspecting the supplying state of inert gas supplied to any container (4) in an article storage facility including inert gas supplying portions (F) for supplying inert gas (an example of clean gas) to inside the containers (4) stored in storage sections (9). Each inert gas supplying portion (F) includes supply nozzles (53N) for injecting inert gas to inside a container (4) with the supply nozzles (53N) provided to a receiving support portion (15) for supporting a container (4) in a storage section (9). The inspecting device (1) includes inspection-purpose intake openings (1G) that come into contact with the supply nozzles (53N) when the inspecting device (1) is supported by the receiving support portion (15), flow meters (101), and inspection-purpose lines (103) each of which connects inspection-purpose intake openings (1G) to the corresponding flow meter (101). And when performing an inspection, with the receiving support portion (15) supporting the inspecting device (1) instead of a container (4), the flow rate of the inert gas that flows into the inspection-purpose lines (103) through the inspection-purpose intake openings (1G) from the supply nozzles (53N) is measured with the flow meters (101). This makes it possible to estimate the flow rate of inert gas supplied to inside a container (4) supported by the receiving support portion (15), based on the measured flow rate of the inert gas.

With the arrangement of Patent Document 1, when the inert gas is supplied to inside a container (4), the inert gas ejected from the supply nozzles (53N) flows to inside the container (4) through the intake openings (4G) with the intake openings (4G) provided to the container (4) in contact with the supply nozzles (53N) under the weight of the container (4). Therefore, the flow rate of the inert gas supplied to inside the container (4) can vary depending on how firm the contact is between the intake openings (4G) and the supply nozzles (53N) (that is, depending on the degree of air-tightness (to the exterior area) of the contact areas). In the arrangement of Patent Document 1, containers (4), each of which can hold a plurality of substrates, are used; thus, the total weight of a container (4) can change depending on the number of the substrates held in it. As the total weight of the container (4) changes, the firmness of the contact between the intake openings (4G) and the supply nozzles (53N) also changes. In light of this issue, in the arrangement of Patent Document 1, by providing inspecting device (1) with weight support portions each of which can support one or more weights for adjusting the total weight of the inspecting device (1), the firmness of the contact between the inspection-purpose intake openings (1G) and the supply nozzles (53N) can be adjusted by means of weights to match the firmness of the contact between the intake openings (4G) and the supply nozzles (53N) which changes depending on the state (i.e., the number) of the substrates held within a container (4). This makes it possible to obtain a flow rate of the inert gas measured by the flow meter (101) that has a value that is close to the flow rate of the inert gas actually supplied to inside a container (4) regardless of the number of substrates held in the container (4).

SUMMARY OF THE INVENTION

Incidentally, the clean gas, that is supplied to inside a container from an intake portion, such as the intake openings, is released through an outlet portion, such as the outlet openings, or through any gaps, etc., to outside the container. Thus, the magnitude of the inflow resistance (pressure loss) of the container, which is the resistance to the flow of clean gas as the clean gas is allowed to flow into the container through the intake portion, depends on the magnitude of the outflow resistance the gas experiences as it is released through the outlet portion and on the degree of air-tightness of the container, etc. Generally, in addition to the firmness of the contact between the intake portion of a container and an ejecting portion of clean gas, the magnitude of the inflow resistance of the container also has a large impact on the flow rate of the clean gas supplied to the inside the container. In light of this issue, it is conceivable to design the flow measuring device by taking into consideration the magnitude of the inflow resistance of the container to which the clean gas is supplied, to obtain the measured flow rate of the clean gas measured that has a value that is close to the flow rate (referred to, hereinafter, as the "actual supply flow rate") of the clean gas actually supplied to inside the container. However, the magnitude of the inflow resistance of a container may vary depending on the kind (type) and the manufacturer of the container. And the inflow resistance may vary even among the same kind or type of containers due to individual differences and changes that occur over time, etc. Thus, if a flow measuring device that is designed as described above is used, it may be possible to obtain a measured flow rate of the clean gas that has a value close to the actual supply flow rate of a container which has a certain specific inflow resistance. However, for another container for which the magnitude of inflow resistance is different from one for the container for which the flow measuring device is designed, the difference between the flow rate of clean gas measured with the flow measuring device and the actual supply flow rate tends to be significant. In other words, even if a flow measuring device that is designed as described above is used, if there are variations in inflow resistance among the containers to which the clean gas is supplied, it is not easy to estimate the flow rate of clean gas supplied to inside a container with sufficient accuracy for each of the containers among which the inflow resistance is different. However, this issue was not specifically recognized in Patent Document 1.

Thus, it is desirable to provide a flow measuring device with which, even when there are variations in inflow resistance among containers, the flow rate of clean gas supplied to inside a container can be estimated with sufficient accuracy for each of containers among which inflow resistance may be different.

A flow measuring device, in accordance with the present invention, is used to inspect a clean gas supplying device that includes one or more support members each configured to support a container, an ejecting portion provided to each of the one or more support members and configured to eject clean gas to inside a container supported by corresponding one of the one or more support members. The flow measuring device is configured to measure a flow rate of clean gas ejected from the ejecting portion when the flow measuring device is supported by a support member. The flow measuring device comprises an intake portion configured to be connected to the ejecting portion, one or more gas lines each of which is connected to the intake portion and which is configured to allow gas ejected from the ejecting portion to flow therein, one or more flow meters each of which is configured to measure a flow rate of gas that flows through corresponding one of the one or more gas lines, at least one resisting member configured to provide resistance to flow of gas in at least one of the one or more gas lines, a main body portion which includes one or more supported portions each configured to be supported by the support member, the main body portion being configured to support the intake portion, the one or more gas lines, the one or more flow meters, and the at least one resisting member wherein a magnitude of the resistance provided by the at least one resisting member is adjustable.

By using the flow measuring device so arranged and by placing the flow measuring device on a support member so that the ejecting portion and the intake portion are connected, or in contact, with, each other, clean gas ejected from the ejecting portion can be allowed to flow into the one or more gas lines from the intake portion. The flow rate measured by the one or more flow meters under this condition depends on the inflow resistance of the flow measuring device, which is the resistance to the flow of clean gas as the clean gas is allowed to flow into the one or more gas lines through the intake portion. That is, the flow rate measured by the one or more flow meters has a value that is close to the flow rate of clean gas supplied to inside a container when the container supported by a support member has an inflow resistance that is comparable in magnitude to the inflow resistance of the flow measuring device. As a result, the flow rate of clean gas supplied to inside a container that has an inflow resistance that is comparable in magnitude to the inflow resistance of the flow measuring device can be estimated accurately based on the flow rate measured by the one or more flow meters.

And since the magnitude of the resistance provided by the at least one resisting member is adjustable in the arrangement described above, the magnitude of the inflow resistance of the flow measuring device can be changed by adjusting the magnitude of the resistance provided by the at least one resisting member. Thus, the flow rate of the clean gas supplied to inside a container can be estimated accurately not only for containers that have inflow resistance of a certain magnitude but also for containers that have inflow resistance that is within a range over which the inflow resistance of the flow measuring device can be adjusted. That is, even when there are variations in the inflow resistance among the containers, the flow rate of the clean gas supplied to inside a container can be estimated accurately for each of a plurality of containers having mutually different inflow resistance by taking measurements using one flow measuring device.

As such, with the arrangement described above, a flow measuring device can be provided with which, even when there are variations in the inflow resistance among the containers, the flow rate of the clean gas supplied to inside a container can be estimated accurately for each of a plurality of containers having mutually different inflow resistance.

BRIEF DESCRIPTION OF THE DRAWINGS

FIG. 8 is a plan view of the resistance providing device.

DETAILED DESCRIPTION OF EMBODIMENTS

Embodiments of a flow measuring device and a flow measuring system are described with reference to the drawings. In the present embodiment, an example is described in which the clean gas supplying devices 30 to be inspected by the flow measuring device and the flow measuring system are provided in a container storage facility 100 as shown in FIG. 1.

Figure 1:
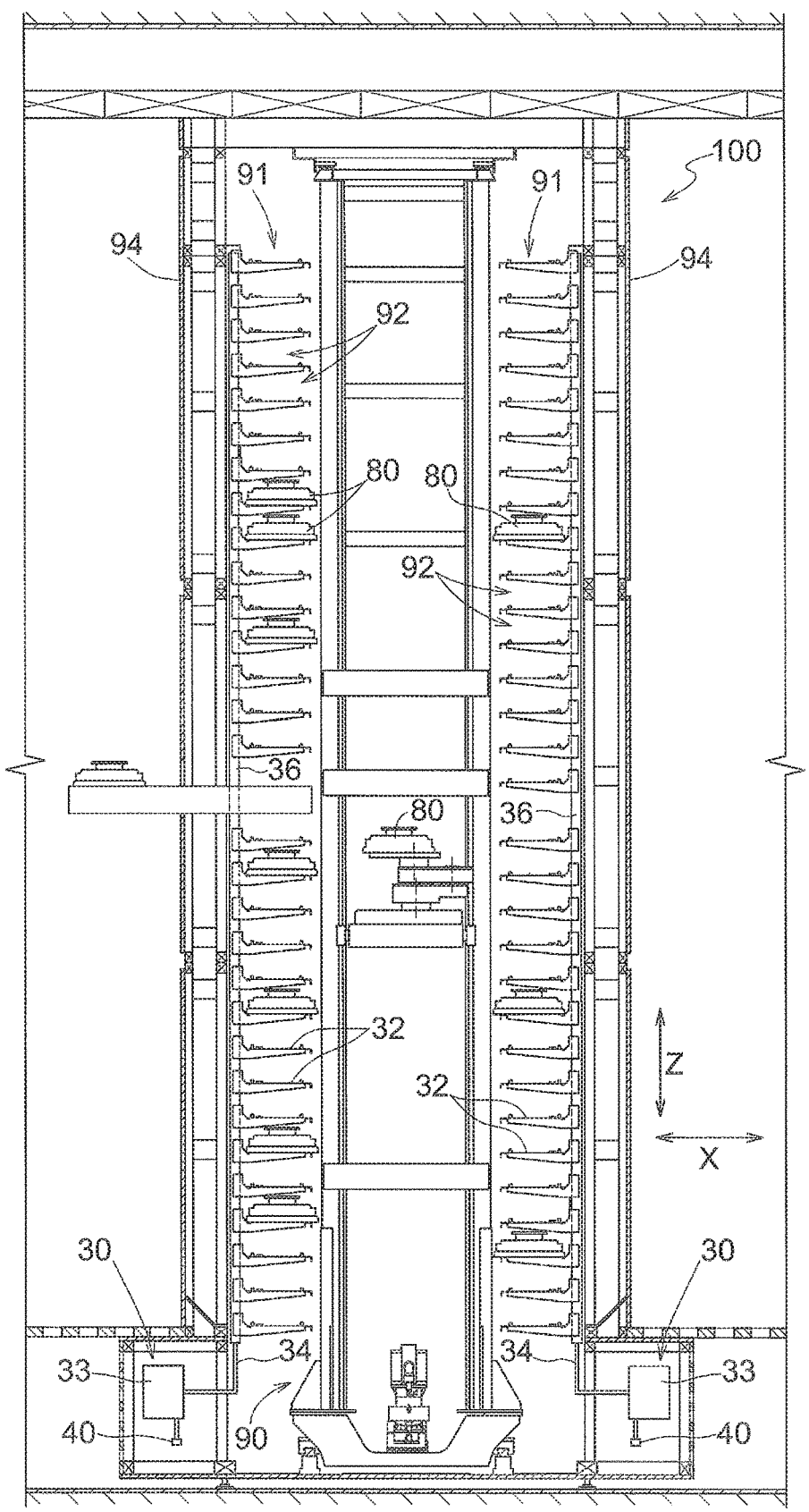
FIG. 1 is a side view of a vertical cross-section of a container storage facility.
Figure 2:
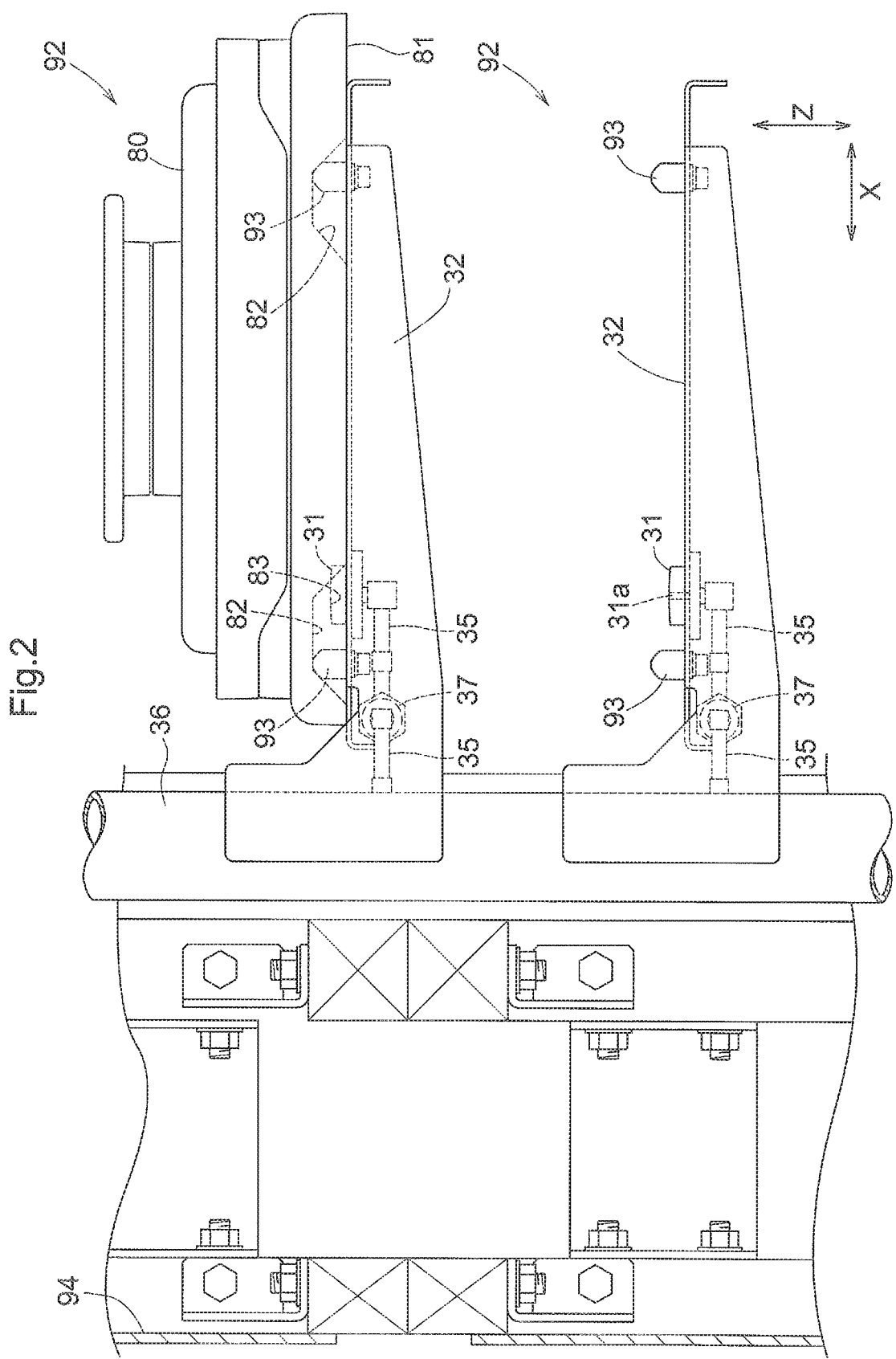
FIG. 2 is a side view of storage sections.
Figure 3:
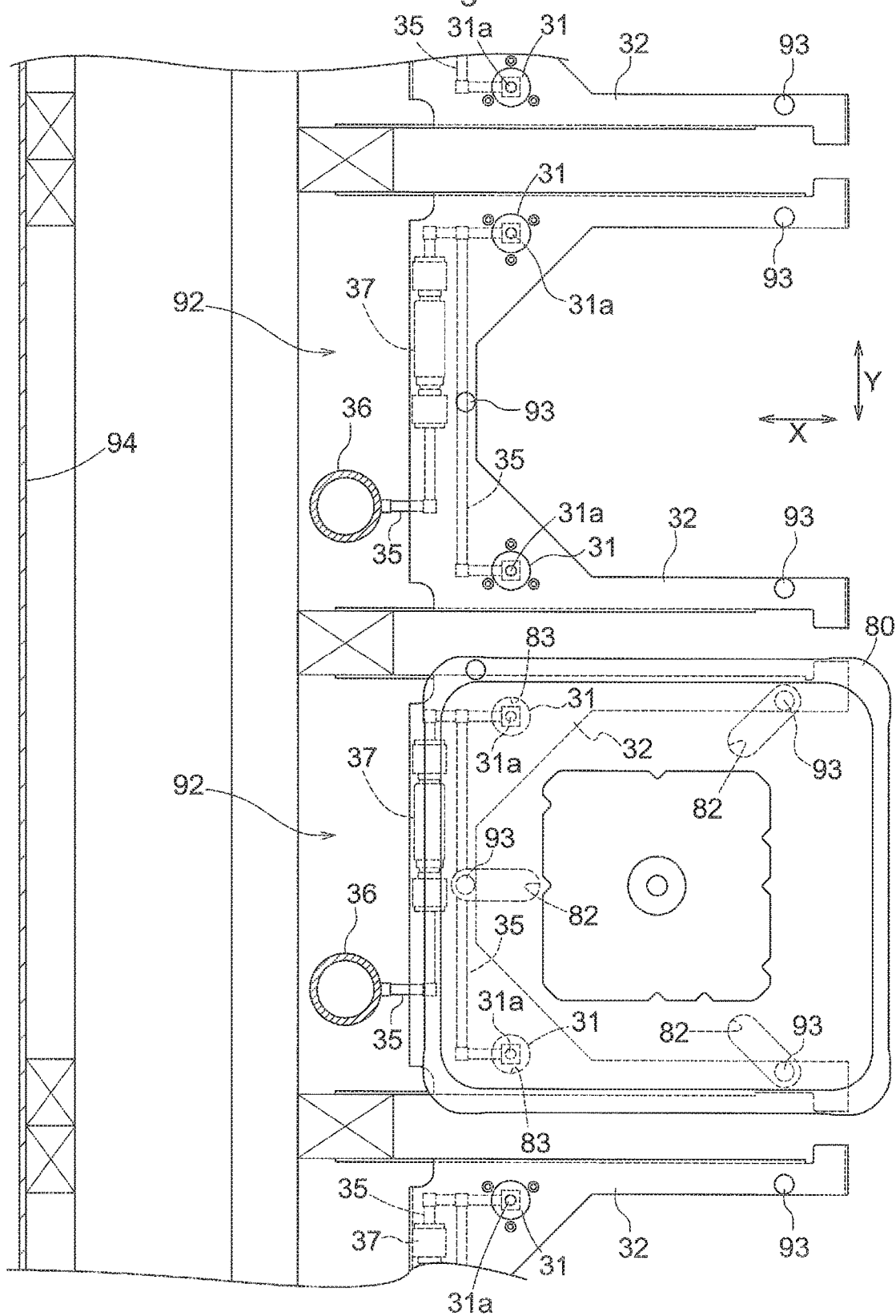
FIG. 3 is a plan view of storage sections.

As shown in FIG. 1, the container storage facility 100 in accordance with the present embodiment includes storage racks 91 each of which is configured to store containers 80, a container transport device 90 configured to transport the containers 80, one container 80 at a time, and clean gas supplying devices 30 each of which is configured to supply clean gas (purge gas) to each container 80 stored in the storage racks 91. As shown in FIGS. 1-3, each storage rack 91 includes a plurality of storage sections 92 each of which is configured to store a container 80, with the storage sections 92 being arranged one storage section 92 next to another along a second horizontal direction Y and one storage section 92 above another in a vertical direction Z. Here, the second horizontal direction Y is a horizontal direction that is along a lateral direction (rack lateral direction) of the storage rack 91. Each storage section 92 includes a support member 32 for supporting a container 80. Each container 80 can be stored in a storage section 92 having a support member 32 with the container 80 supported by the support member 32. In the present embodiment, a pair of storage racks 91 are so located that they face each other along a first horizontal direction X, with a travel path of the container transport device 90 located therebetween. Here, the first horizontal direction X is a horizontal direction that is along a front and back direction (rack front and back direction) of the storage rack 91, and is perpendicular to the second horizontal direction Y.

In the present embodiment, each support member 32 is configured to support a container 80 from below. More specifically, as shown in FIG. 3, each support member 32 is generally formed to have a U-shape as seen along the vertical direction Z, and is configured to support a peripheral area of the bottom surface 81 of the container 80. Each support member 32 is supported by a frame of a storage rack 91 in a cantilever fashion, as a result of the fact that its one end portion (portion that corresponds to the bottom portion of the U-shape) along the first horizontal direction X is fixed to the frame of the storage rack 91. As shown in FIGS. 2 and 3, each support member 32 is provided with positioning projections 93 (positioning pins). Each projection 93 is formed to project upward from the top surface (which is a portion that is generally flat) of the support member 32. Each support member 32 is provided with a plurality of projections 93 (three projections 93 in the present embodiment). The projections 93 are formed at three locations with one in the bottom portion of the U-shape and one in each of the two end portions.

As shown in FIG. 2, recessed portions 82 each having a shape that is recessed upward is formed in the bottom surface 81 of each container 80. The same number of recessed portions 82 as the number of the projections 93 are formed. And in the present embodiment, three recessed portions 82 are formed in the bottom surface 81 of the container 80. Each container 80 can be supported by a support member 32 with the container properly positioned with respect to the support member 32 as a result of each projection 93 engaging the corresponding recessed portion 82. The inner surfaces of the recessed portion 82 are sloped surfaces so that, when placing the container 80 on a support member 32, even if the position of the container 80 is horizontally displaced from the proper position with respect to the support member 32, the horizontal position of the container 80 is corrected to the proper position with respect to the support member 32 as a result of the fact that the projections 93 are guided by the inner surfaces of the corresponding recessed portions 82. In the present embodiment, each container 80 is a reticle pod configured to hold one or more reticles (photomasks) for EUV (extreme ultraviolet) lithography.

The container transport device 90 can move along the second horizontal direction Y in front of each storage rack 91 to transport containers 80, one container 80 at a time, to a storage section 92 or from a storage section 92. In the present embodiment, the container transport device 90 can move along the second horizontal direction Y between the pair of storage racks 91. In the present embodiment, the container transport device 90 is a stacker crane. While not described in detail, the container transport device 90 transports a container 80 being carried into the storage rack 91 from a transfer location for carrying-in operation to a storage section 92. And it transports a container 80 to be carried out of the storage rack 91 from the storage section 92 in which the container 80 is stored to the same transfer location for carrying-out operation which also functions as the aforementioned transfer location for carry-in operation, or to a transfer location for carrying-out operation which is provided separately from the aforementioned transfer location for carry-in operation.

In the present embodiment, the container storage facility 100 is installed in a clean room of a down-flow type in which clean air flows downward from the ceiling side toward the floor side. In the present embodiment, the container storage facility 100 includes walls 94 that surround the side perimeter (perimeter as seen along a vertical direction) of a space (hereinafter "installation space") in which the storage racks 91 and the container transport device 90 are located. Each wall 94 is formed by a member that does not have any holes formed in it. Clean air that is caused to flow into the installation space from the ceiling side flows downward within the installation space together with any clean gas ejected from the ejecting portions 31 described below (including the clean air that is released from containers after it is ejected from the ejecting portions into the containers), and thereafter, is released from one or more locations near the floor portion and out to the space outside the installation space.

Figure 4:
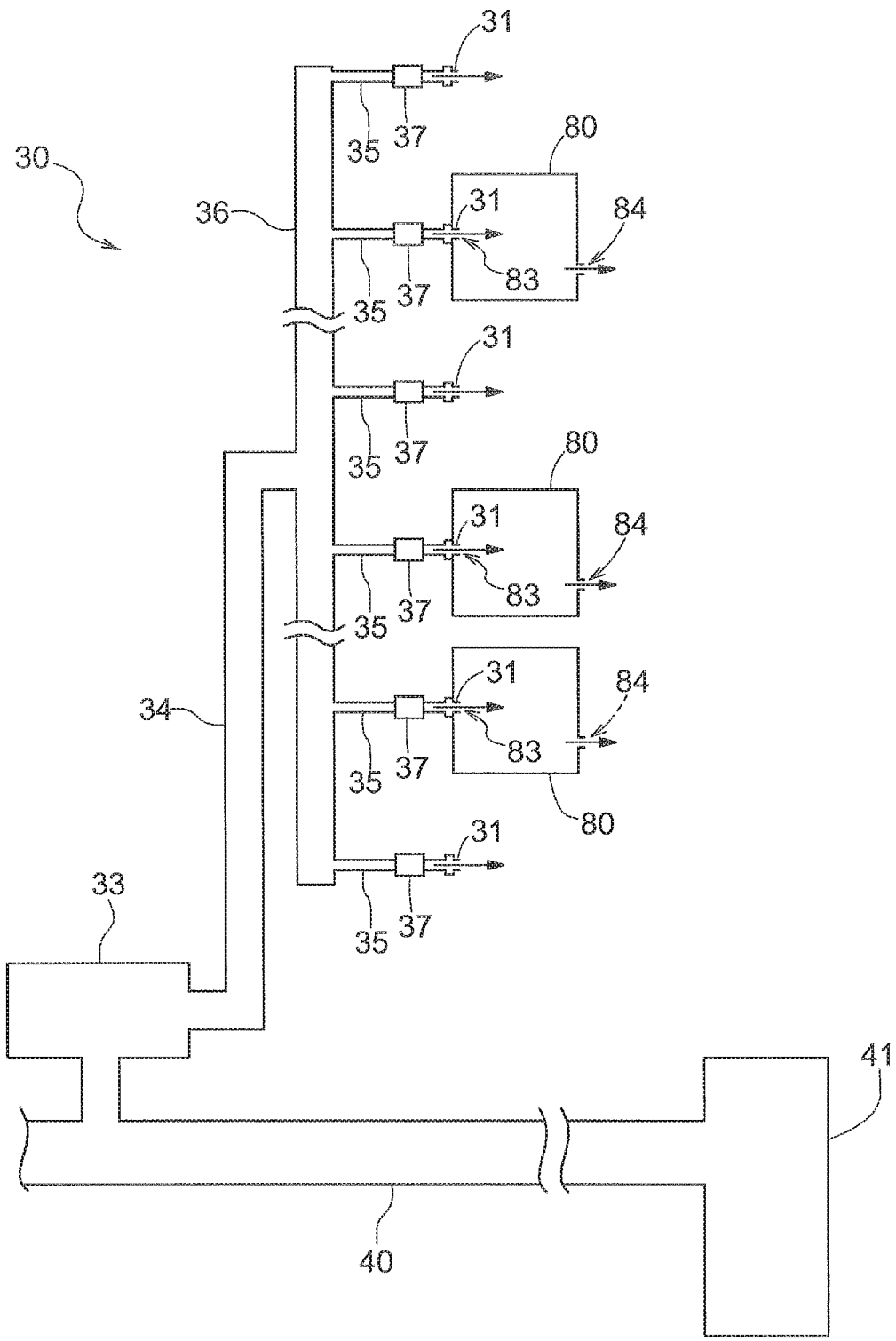
FIG. 4 is a diagram of a clean gas supplying device.

As shown in FIGS. 2-4, each clean gas supplying device 30 includes the support members 32 each of which is configured to support a container 80, and an ejecting portion 31 which is configured to eject clean gas to inside a container 80 supported by a support member 32. An ejecting portion 31 is provided to each support member 32 (i.e., each support member 32 has its own ejecting portion 31). In the present embodiment, the clean gas supplying device 30 includes a plurality of support members 32; and an ejecting portion 31 is provided to each of the plurality of support members 32 (i.e., each of the plurality of support members 32 is provided with its own ejecting portion 31) to eject clean gas to inside, or into, the container 80 supported by the support member 32. In the present embodiment, the clean gas supplying devices 30 are installed in the container storage facility 100 to supply clean gas to inside a container 80 stored in each of the plurality of storage sections 92. Thus, in the present embodiment, each clean gas supplying device 30 uses the support member 32 provided to each storage section 92 as a support member for supporting a container 80 to which clean gas is supplied. Seen from a different perspective, the support members 32 which the clean gas supplying device 30 has are also used to support containers 80 in the storage sections 92. Note that the clean gas may be, for example, inert gas, such as nitrogen gas, or clean dry air from which dust, debris and moisture are removed. In the present embodiment, clean gas is inert gas.

As shown in FIG. 4, in the present embodiment, the clean gas supplying device 30 includes a primary gas line 34 through which clean gas is supplied from the supply source 41 of clean gas, a flow control device 33 (mass flow controller) configured to control the flow rate of clean gas which flows through the primary gas line 34, and a plurality of branch gas lines 35 each of which branches off from the primary gas line 34 at a location downstream of the flow control device 33, and each of which is connected to the corresponding ejecting portion 31. Note that, in the present embodiment, each gas line (or simply a line) is a pipe made of resin or any suitable metal. As shown in FIG. 3, in the present embodiment, each ejecting portion 31 includes a plurality of eject openings 31*a*, more specifically two eject openings 31*a*. That is, with an eject opening forming member being a member that forms an eject opening 31*a*, each ejecting portion 31 consists of a group of eject opening forming members located at mutually different locations (two different locations in the present embodiment) in the support member 32. As shown in FIG. 3, each eject opening forming member is generally formed to have a shape of a circular disk in plan view (i.e., as seen along a vertical direction), and its eject opening 31*a* is formed in the center of the circular disk. A downstream-side portion of a branch gas line 35 is connected to each of the eject openings 31*a* of an ejecting portion 31, so that clean gas is ejected or discharged from each of the eject openings 31*a*. In the present embodiment, a filter 37 for removing dust and debris from the clean gas is provided in each of the branch gas line 35. And clean gas is ejected from each eject opening 31*a* after the dust and debris are removed from the clean air by the filter 37.

As shown in FIGS. 2-4, intake openings (third intake openings 83) and an outlet opening 84 are provided to each container 80. Note that the intake openings provided to a container 80 are referred to as the third intake openings 83 to distinguish them from first intake openings 11*a*, and second intake openings 21*a* described below. As shown in FIG. 2, each third intake opening 83 is formed in the bottom surface 81 of a container 80. And while not shown, an outlet opening 84 is also formed in the bottom surface 81 of the container 80. While not described in detail, each of the third intake openings 83 and the outlet opening 84 is formed to extend through, along the vertical direction Z, a grommet provided in the bottom surface 81 of the container 80. With a container 80 supported by the support member 32, the third intake openings 83 come into contact with and become connected to the ejecting portion 31 provided to the support member 32, which allows clean gas ejected from the ejecting portion 31 to flow to inside the container 80 through the third intake openings 83. In the present embodiment, the same number of third intake openings 83 as the number (two in the present embodiment) of the eject openings 31a provided to each ejecting portion 31 are formed in the bottom surface 81 of each container 80. With a container 80 supported by a support member 32, each of the third intake openings 83 is connected to the corresponding eject opening 31a and the clean gas flows into the container 80 through each of the third intake openings 83.

Each third intake opening 83 is provided with an intake opening and closing valve (not shown) whereas each outlet opening 84 is provided with an outlet opening and closing valve (not shown). Each of the intake opening and closing valve and the outlet opening and closing valve is urged by an urging member, such as a coil spring, to its closed state or toward its closed position. When clean gas is ejected from the ejecting portion 31 with the ejecting portion 31 (eject openings 31a) connected to the third intake openings 83, each intake opening and closing valve is opened by that pressure, allowing the clean gas to be supplied to inside the container 80 through the third intake openings 83. In addition, when the pressure inside the container 80 becomes high as a result of clean gas being supplied into the container 80, the outlet opening and closing valve is opened by that pressure, causing gas inside the container 80 (air, humid air, and clean gas already supplied to the container 80) to be released from the outlet opening 84. Note that the container 80 is configured to be airtight or sealed. Thus, arrangements are made such that clean gas inside a container 80 would not leak to outside easily when ejecting portion 31 and the third intake openings 83 are disconnected when transporting the container 80 with the container transport device 90.

The flow rate of the clean gas supplied to inside a container 80 (i.e., sum total of the flow rate of clean gas supplied into the container 80 through each of the third intake openings 83 in the present embodiment) depends on the inflow resistance of the container 80. Here, the inflow resistance of the container 80 is the resistance (pressure loss) to the flow of clean gas as the clean gas is allowed to flow into a container 80 through the third intake openings 83. The inflow resistance of a container 80 depends on, among other factors, the urging force of each of the intake opening and closing valves and the outlet opening and closing valve, and on the degree of air-tightness of the container 80.

As shown in FIG. 4, in the present embodiment, clean gas is supplied to the primary gas line 34 from the supply source 41 of clean gas through a main line 40. In addition, in the present embodiment, the clean gas supplying device 30 includes a relay gas line 36 which is located in a portion where branch gas lines 35 branch off from the primary gas line 34. And the upstream end portion of each of the plurality of branch gas lines 35 is connected to the relay gas line 36 whereas the relay gas line 36 is connected to the downstream end portion of the primary gas line 34. Here, the group of the ejecting portions 31 to which the branch gas lines 35 that branch out from the same primary gas line 34 are connected will be referred to as an "ejecting portion group". The group of support members 32 to which the group of ejecting portions 31 are provided will be referred to as a "support member group". And the group of storage sections 92 in which the group of support members 32 are provided will be referred to as a "storage section group". In the present embodiment, the plurality of storage sections 92 that belong to the same storage section group are a plurality of storage sections 92 that are in the same vertical row or column (i.e., a plurality of storage sections 92 that overlap each other as seen along the vertical direction Z). As shown in FIG. 1, each relay gas line 36 is so arranged to extend along the vertical direction Z over the area or range over which a plurality of storage sections 92 belonging to the same storage section group are located.

The flow control device 33 is provided at an intermediate location of the primary gas line 34, and has an inflow port which is connected to a portion of the primary gas line 34 that is upstream of the flow control device 33, and an eject port which is connected to a portion of the primary gas line 34 that is downstream of the flow control device 33. Further, the flow control device 33 includes an internal passage which connects the inflow port to the eject port, a flow rate adjusting valve which adjusts the flow rate of the gas flowing through the internal passage toward the eject port side, a flow rate sensor which measures the flow rate of the gas flowing through the internal passage, and an internal controller which controls the operation of the flow rate adjusting valve. By controlling the operation of the flow rate adjusting valve depending on a flow rate command outputted from a control device (not shown) configured to control the operation of the clean gas supplying device 30, the flow control device 33 (more specifically the internal controller) controls the flow rate (volume of flow per unit amount of time) of the clean gas that flows through the primary gas line 34 to cause the flow rate to match the value specified by the flow rate command. Thus, in the present embodiment, the flow control device 33 is provided to the primary gas line 34 instead of to the branch gas lines 35. Thus, when the flow rate of the clean gas in the portion on the downstream side of the flow control device 33 in the primary gas line 34 is greater than zero, clean gas is ejected not only from ejecting portions 31 that are connected to the third intake openings 83 of the containers 80 but also from ejecting portions 31 that are not connected to the third intake openings 83 of the containers 80. That is, clean gas is ejected from all the ejecting portions 31 that form one or more ejecting portion groups that are on the downstream side of the flow control device 33 in a primary gas line 34.

Figure 5:
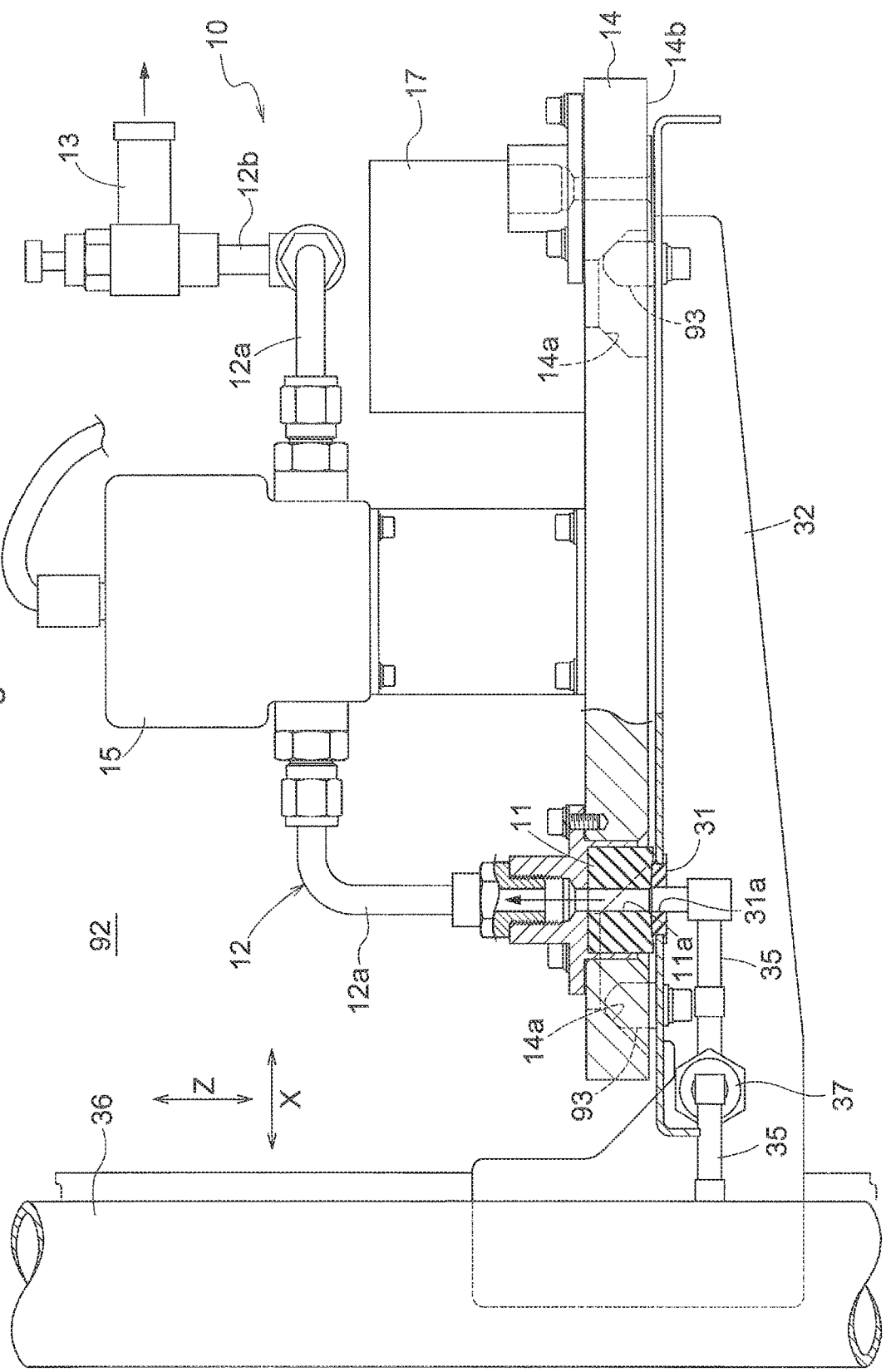
FIG. 5 is a side view of a flow measuring device.
Figure 6:
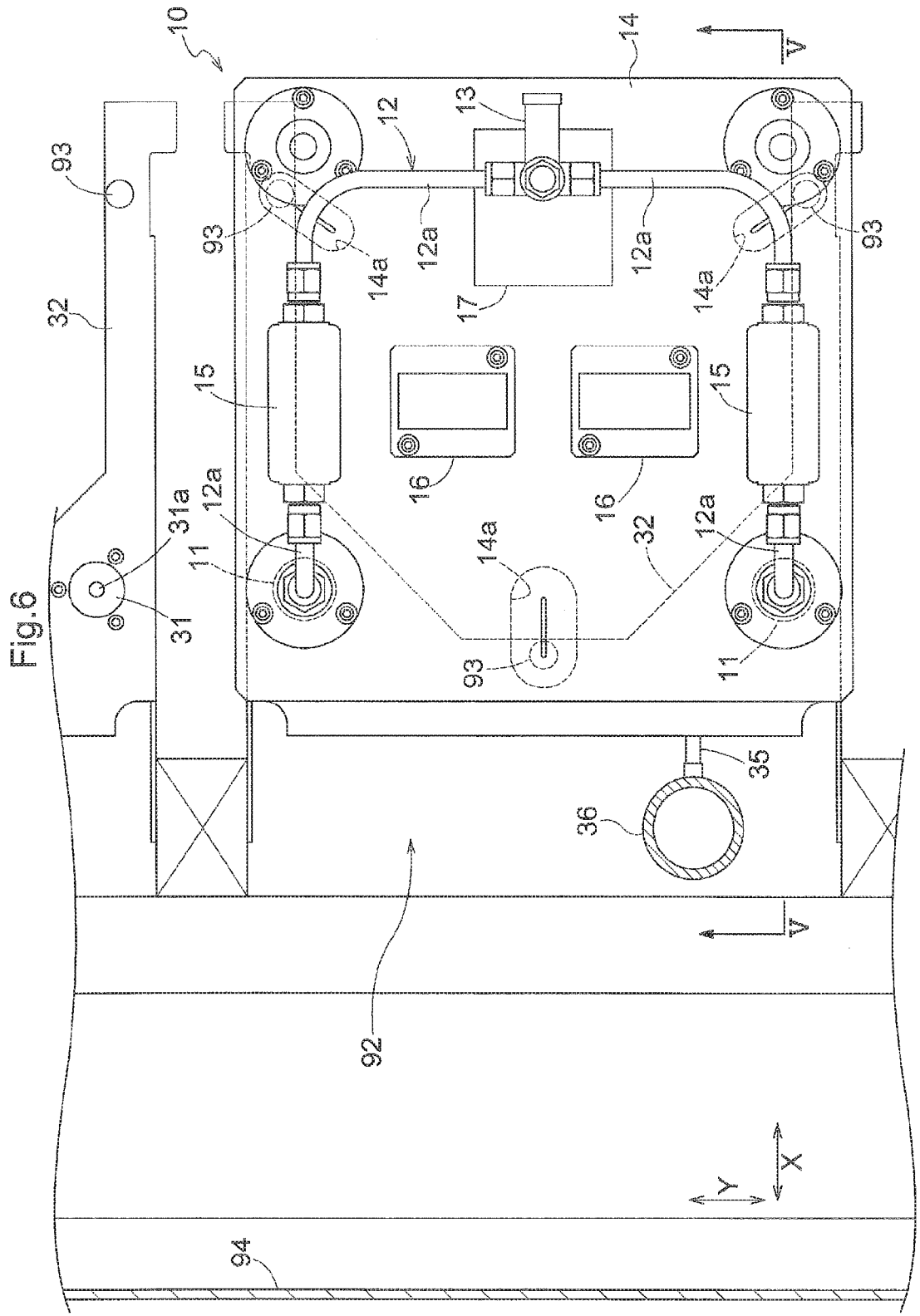
FIG. 6 is a plan view of the flow measuring device.

A flow measuring device 10 used to inspect the clean gas supplying device 30, and a flow measuring system used to inspect the clean gas supplying device 30 are described next. The flow measuring device 10 is incorporated in the flow measuring system. The flow measuring device 10 is a device that measures the flow rate (the volume of flow per unit amount of time) of clean gas that is ejected from the ejecting portion 31, when supported by a support member 32. In the present embodiment, the flow measuring device 10 and each resistance providing device 20 described below are configured to be supported by any support member 32 from below. As described below, the flow rate of the clean gas supplied to inside a container 80 supported by a support member 32 through the ejecting portion 31 can be estimated by taking a measurement using the flow measuring device 10. As shown in FIGS. 5 and 6, the flow measuring device 10 includes a first intake portion 11 which is configured to be connected to the ejecting portion 31 when the flow measuring device 10 is supported by a support member 32, first gas lines 12 connected to the first intake portion 11, flow meters 15 configured to measuring the flow rate (volume of flow per unit amount of time) of the gas that flows through the first gas lines 12, a first resisting member 13 which provides resistance to the flow of gas within the first gas lines 12, and a first main body portion 14. With the flow measuring device 10 supported by a support member 32, gas ejected from the ejecting portion 31 flows through the first gas lines 12. And the flow rate of gas that flows downstream through the first gas lines 12 is measured by the flow meters 15. In the present embodiment, the first resisting member 13 is located downstream of each flow meter 15 along the direction in which a corresponding portion (first gas line portion 12a described below) of the first gas lines 12 extends (on the opposite side from where the corresponding first gas line is connected to the first intake portion 11). In other words, each flow meter 15 is located upstream of the first resisting member 13 along the direction in which the corresponding portion (first gas line portion 12a described below) of the first gas lines 12 extends (on the side where the corresponding first gas line is connected to the first intake portion 11). In the present embodiment, the first intake portion 11 is, or corresponds to, the "intake portion": the first gas lines 12 are, or correspond to, the "gas lines": the first resisting member 13 is, or corresponds to, the "resisting member": and the first main body portion 14 is, or correspond to, the "main body portion".

The first main body portion 14 has first supported portions 14a each of which is configured to be supported by a support member 32. And the first main body portion 14 is a member that supports the first intake portion 11, the first gas lines 12, the flow meters 15, and the first resisting member 13. Each of the first intake portion 11, the first gas lines 12, the flow meters 15, and the first resisting member 13 is supported by the first main body portion 14 directly or indirectly. In the present embodiment, the first main body portion 14 is a member that has a general shape of a flat plate (i.e., flat and thin); and, the first supported portions 14a are formed in a first bottom surface 14b which is the bottom surface of the first main body portion 14. Each first supported portion 14a is formed in a shape that is recessed upward, in the first bottom surface 14b. The same number of first supported portions 14a as the number of projections 93 provided to each support member 32 are formed. And three first supported portions 14a are formed in the first bottom surface 14b in the present embodiment. The first main body portion 14 is supported by a support member 32 such that it is properly positioned with respect to the support member 32, as a result of the fact that the projections 93 provided to the support member 32 engage the corresponding first supported portions 14a. The concave inner surface of each first supported portion 14a forms one or more sloped surfaces so that, even if the position of the flow measuring device 10 (the first main body portion 14) is horizontally displaced from the proper position with respect to the support member 32 when placing the flow measuring device 10 on a support member 32, the horizontal position of the flow measuring device 10 is corrected to the proper position with respect to the support member 32 as a result of the fact that each projection 93 is guided by the one or more inner surfaces of the corresponding first supported portion 14a. When the flow measuring device 10 is supported by a support member 32, the flow measuring device 10 and the support member 32 are in contact with each other only through the areas of contact between the first supported portions 14a and the projections 93 and the areas of contact between the first intake portion 11 and the ejecting portion 31. In other words, the first main body portion 14 which supports the first intake portion 11, the first gas lines 12, the flow meters 15, and the first resisting member 13 is supported only by the projections 93 and the ejecting portion 31 (and mainly by the projections 93) from below. In the present embodiment, a first supported portion 14a is, or corresponds to, the "supported portion".

As shown in FIG. 5, the first intake portion 11 includes first intake openings 11a each of which is an intake opening configured to be connected to the corresponding eject opening 31a of the ejecting portion 31. Each first intake opening 11a is formed to extend through, along the vertical direction Z, a grommet provided to the first intake portion 11. As described above, in the present embodiment, each ejecting portion 31 includes a plurality of eject openings 31a. And to correspond to this arrangement, each first intake portion 11 includes a plurality of first intake openings 11a each of which is configured to be connected to the corresponding one of the plurality of eject openings 31a. More specifically, the first intake portion 11 includes two first intake openings 11a. That is, with an intake opening forming member being a member (aforementioned grommet in the present embodiment) in which a first intake opening 11a is formed, the first intake portion 11 consists of a group of intake opening forming members located at mutually different locations (two different locations in the present embodiment) in the first main body portion 14. In the present embodiment, a first intake opening 11a is, or corresponds to, an "intake opening".

As described above, in the present embodiment, the first intake portion 11 includes a plurality of first intake openings 11a. And to correspond to this arrangement, the first gas lines 12 include a plurality of first gas line portions 12a each of which is connected to the corresponding one of the plurality of first intake openings 11a. More specifically, the first gas lines 12 include two first gas line portions 12a. In addition, in the present embodiment, the first gas lines 12 also includes a second gas line portion 12b which is connected to an end portion (on the opposite side from the first intake opening 11a) of each of the plurality of first gas line portions 12a (the two first gas line portions 12a in the present embodiment, the same is true with the description below) and in which the gas, that is the combination or mixture of gas that flows through all of the plurality of first gas line portions 12a, flows. In the present embodiment, each of the plurality of first gas line portions 12a has one flow meter 15 provided therein. That is, each of the flow meter 15 is provided in an intermediate location of a first gas line portion 12a that is its target of measurement, to measure the flow rate of the gas that flows through the first gas line portion 12a. The plurality of first gas line portions 12a are formed, or manufactured, such that the length of a first gas line portion 12a from the location at which it is connected to the corresponding first intake opening 11a to the location at which it is connected to the second gas line portion 12b is identical for all first gas line portions 12a. As shown in FIGS. 5 and 6, in the present embodiment, the flow measuring device 10 includes displays 16 for displaying the result of measurement made by the corresponding flow meter 15, and a terminal block 17 on which the cables (battery cables, communication cables, etc.) that are connected to the flow meters 15 and the displays 16 are fixed. These displays 16 and the terminal block 17 are also supported by the first main body portion 14. While not shown, an electric power source such as a battery etc., for supplying operating power to the flow meters 15 and the displays 16 is also supported by the first main body portion 14.

The first resisting member 13 is configured such that the magnitude of the resistance (resistance to the flow of gas in the first gas lines 12) is adjustable. As described above, the first gas lines 12 includes a plurality of first gas line portions 12a in the present embodiment; and, the first resisting member 13 is provided to provide resistance to the flow of gas in each of the plurality of first gas line portions 12a. In the present embodiment, the first resisting member 13 is provided to the second gas line portion 12b. This arrangement makes it possible to adjust resistance for (resistance to the gas that flows through) each of the plurality of first gas line portions 12a by adjusting the first resisting member 13. As described above, in the present embodiment, the plurality of first gas line portions 12a are formed, or manufactured, such that the length of each first gas line portion 12a is identical for all first gas line portions 12a. Thus, the resistance of each of the plurality of first gas line portions 12a has an identical or comparable magnitude to any other. In addition, in the present embodiment, the first resisting member 13 is a speed control valve (speed controller) which can adjust the flow rate of gas flowing downstream therefrom, and is configured such that the magnitude of the resistance can be adjusted by manually operating a member such as a finger-operable bow etc. As a result of the fact that the flow rate of gas flowing downstream is restricted to a value less than or equal to a specified value (adjustment value) at the location of the first resisting member 13 in a portion (second gas line portion 12b) of the first gas lines 12, resistance is provided to the flow of gas that flows within the portions of the first gas lines 12 that are upstream of the location of the first resisting member 13.

By placing the flow measuring device 10, that has the structure described above, on a support member 32, the clean gas ejected from the ejecting portion 31 can be allowed to flow into the first gas lines 12 through the first intake portion 11. In the present embodiment, clean gas ejected from each of the eject openings 31a flows into a first gas line portion 12a through the first intake opening 11a to which the eject opening 31a is connected. In the present embodiment, the total weight of the flow measuring device 10 is set based on the weight of a container 80 such that the firmness of the contact between an ejecting portion 31 (eject opening forming members) and the first intake portion 11 (grommets in each of which a first intake opening 11a is formed) when the flow measuring device 10 is supported by a support member 32 is approximately the same as, or comparable to, the firmness of the contact between the ejecting portion 31 (eject opening forming members) and the third intake openings 83 (grommets in each of which a third intake opening 83 is formed) when the container 80 is supported by the support member 32. In the present embodiment, since each container 80 is a reticle pod configured to hold one or more reticles, the total weight of the flow measuring device 10 is set to be identical to the total weight of a container 80 that holds one reticle, for example.

When the flow measuring device 10 is placed on and supported by a support member 32, the flow rate measured by the flow meters 15 depends on the inflow resistance of the flow measuring device 10. Here, the inflow resistance of the flow measuring device 10 is the resistance (pressure loss) to the flow of clean gas as the clean gas is allowed to flow into the first gas lines 12 through the first intake portion 11. In the present embodiment, the first intake portion 11 (the first intake openings 11a) of the flow measuring device 10 is not provided with any valves that correspond to the intake opening and closing valves provided in the third intake openings 83 of a container 80. Therefore, the inflow resistance of the flow measuring device 10 depends mainly on the magnitude of the resistance that the first resisting member 13 provides to the flow of gas within the first gas lines 12. When a container 80 having an inflow resistance of magnitude comparable to the inflow resistance of the flow measuring device 10 is supported by a support member 32, the flow rate measured by the flow meters 15 (sum total of the flow rate measured by each of the flow meters 15 in the present embodiment) is a value close to the flow rate of clean gas supplied to inside the container 80 from the ejecting portion 31. Therefore, the flow rate of clean gas supplied to inside a container 80, that has the inflow resistance of magnitude comparable to the inflow resistance of the flow measuring device 10, can be estimated accurately based on the flow rate measured by the flow meters 15.

Incidentally, the magnitude of the inflow resistance of a container 80 may vary depending on the kind (type) and the manufacturer of the container. And the inflow resistance may vary even among the same kind or type of containers due to individual differences and changes that occur over time, etc. The magnitude of the inflow resistance of any one container 80 may vary among different containers, because of, for example, variations that may occur in the urging force of the intake opening and closing valve or the outlet opening and closing valve described above, and because of the differences in the airtightness that may occur among different containers 80. With regard to this issue, the flow measuring device 10 includes the first resisting member 13 with which the magnitude of the resistance provided to the flow of gas within the first gas lines 12 can be adjusted; thus, the inflow resistance of the flow measuring device 10 can be adjusted by adjusting the magnitude of the resistance that the first resisting member 13 provides. Therefore, even when there are variations in the inflow resistance among different containers 80, by adjusting the magnitude of the inflow resistance of the flow measuring device 10 to match the inflow resistance of a particular container 80 selected as the container 80 for which the flow rate of clean gas is to be estimated (i.e. as the target of estimation of flow rate), it is possible to obtain the flow rate measured by the flow meters 15 that has a value close to the flow rate of the clean gas supplied from the ejecting portion 31 to inside the selected container 80. In other words, even when there are variations in the inflow resistance among different containers 80, it is possible to accurately estimate the flow rate of the clean gas supplied to inside a container 80 for each of a plurality of containers 80 for which the inflow resistance is different from each other, based on measurements made using one flow measuring device 10. Note that, when the flow rate of clean gas supplied to inside a container 80 from the ejecting portion 31 differs substantially depending on, among other possibilities, the support member 32 that supports the container 80, information on the range of variation in the flow rate of the clean gas supplied to inside the container 80 (range of variation caused by different support members 32 that support the container 80) can be obtained by repeatedly taking measurements with the flow meters 15 while changing the support member 32 that supports the container 80 to different ones.

In the present embodiment, as described above, the flow control device 33 is provided to the primary gas line 34 instead of to the branch gas lines 35. And since branch gas lines 35 are in communication with each other through the relay gas line 36 as shown in FIG. 4, the flow rate of clean gas ejected from an ejecting portion 31 is subject to the effect of the flow rates of clean gas ejected from other ejecting portions 31 that belong to the same ejecting portion group. Although it is conceivable to provide an orifice in each of the branch gas lines 35 to eliminate this effect to the extent possible, it would still be difficult to eliminate this effect completely. Therefore, the flow rate of clean gas supplied to inside a container 80 supported by a support member 32 may change depending not only on the magnitude of the inflow resistance of that container 80 but also on whether any containers 80 are supported by other support members 32 that belong to the same support member group, and on the magnitudes of the inflow resistance of the containers 80 supported by other support members 32 that belong to the same support member group.

Figure 7:
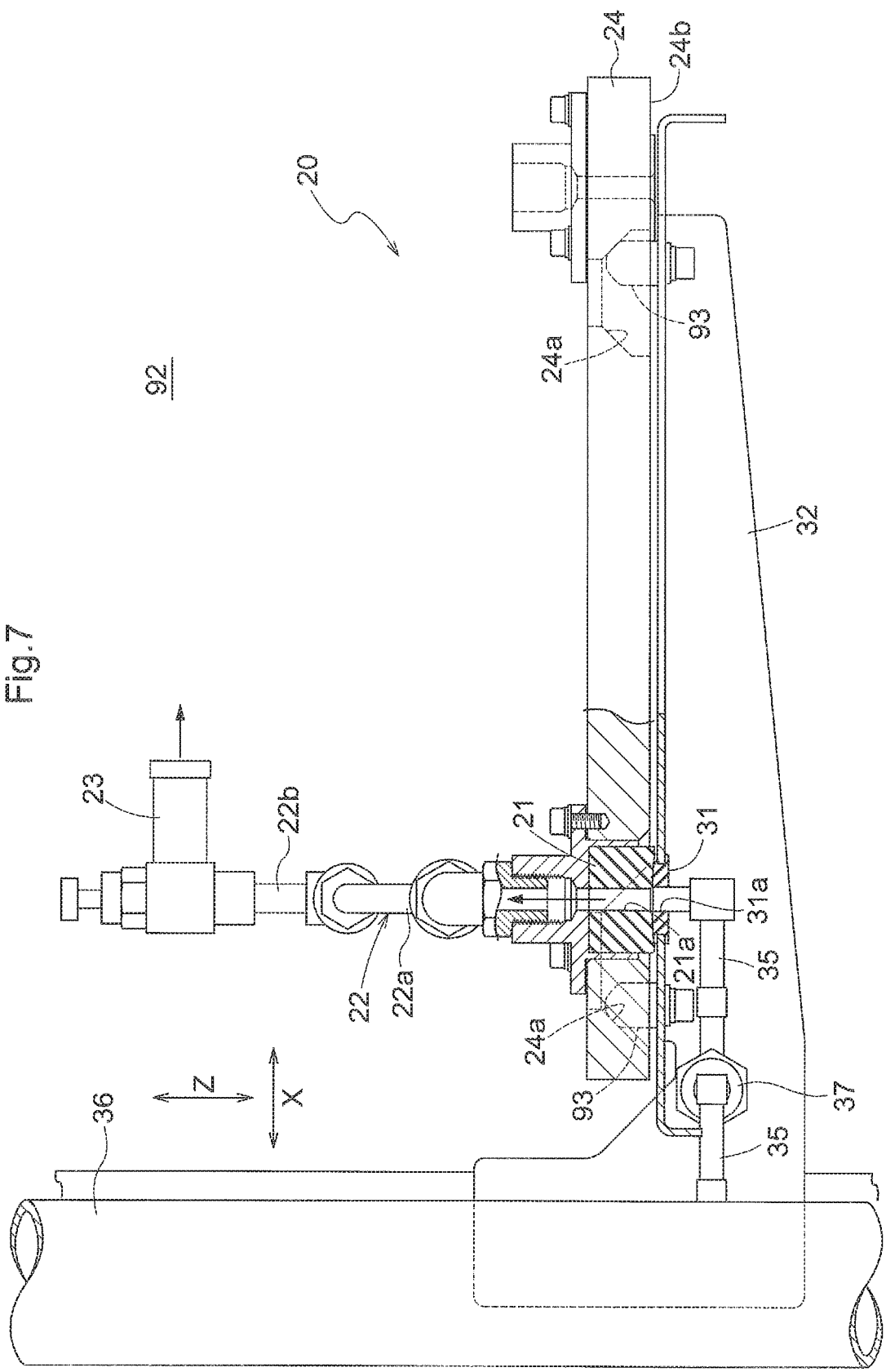
FIG. 7 is a side view of a resistance providing device.

In light of this point, a flow measuring system in accordance with the present embodiment includes one or more resistance providing devices 20, in addition to the flow measuring device 10. The flow measuring system includes a plurality of resistance providing devices 20 in the present embodiment. For example, a flow measuring system includes resistance providing devices 20 the number of which is one less than the number of the ejecting portions 31 that form one ejecting portion group. When making an inspection with the clean gas supplying device 30, the resistance providing devices 20 are placed on, and supported by, the support members 32 (of the plurality of support members 32) that are different from the support member 32 that supports the flow measuring device 10 (i.e., by other support members 32 that belong to the same support member group). As shown in FIGS. 7 and 8, each resistance providing device 20 includes a second intake portion 21 configured to be connected to the ejecting portion 31 when the resistance providing device 20 is supported by a support member 32, second gas lines 22 connected to the second intake portion 21, a second resisting member 23 which provides resistance to the flow of gas in the second gas lines 22, and a second main body portion 24. With the resistance providing device 20 supported by the support member 32, gas ejected from the ejecting portion 31 flows through the second gas lines 22. The second main body portion 24 has second supported portions 24a each of which is configured to be supported by a support member 32. The second main body portion 24 is a member that supports the second intake portion 21, the second gas lines 22, and the second resisting member 23. And the second resisting member 23 is configured such that the magnitude of the resistance (resistance to the flow of gas in the second gas lines 22) is adjustable.

In the present embodiment, each resistance providing device 20 has a structure similar, or identical, to the flow measuring device 10 apart from the fact that it does not have any flow meter 15, the display 16, or the terminal block 17. Thus, while detailed description of the resistance providing device 20 is omitted, the second main body portion 24 has a structure similar, or identical, to the first main body portion 14. And a plurality of second supported portions 24a that correspond to the first supported portions 14a are formed in the second bottom surface 24b which is the bottom surface of the second main body portion 24. And the second main body portion 24 is supported by a support member 32 such that it is properly positioned with respect to the support member 32, as a result of the fact that the projections 93 provided to the support member 32 engage the corresponding second supported portions 24a. The second intake portion 21 has a structure similar, or identical, to the first intake portion 11 and includes a plurality of second intake openings 21a which correspond to the first intake openings 11a. The second gas lines 22 have structures similar, or identical, to the first gas lines 12 apart from the fact that the length and shape of third gas line portions 22a which correspond to the first gas line portions 12a differ from those of the first gas line portions 12a. More specifically, the second gas lines 22 include a plurality of third gas line portions 22a which correspond to the first gas line portions 12a as well as a fourth gas line portion 22b which corresponds to the second gas line portion 12b. The plurality of third gas line portions 22a are formed, or manufactured, such that the length of a third gas line portion 22a from the location at which it is connected to the corresponding second intake opening 21a to the location at which it is connected to the forth gas line portion 22b is identical for all third gas line portions 22a. The second resisting member 23 has a structure similar, or identical, to the first resisting member 13 and is a speed control valve which can adjust the flow rate of gas flowing downstream therefrom in the present embodiment. The second resisting member 23 is provided to the fourth gas line portion 22b which corresponds to the second gas line portion 12b.

In the present embodiment, the total weight of each resistance providing device 20 is set based on the weight of a container 80 such that the firmness of the contact between an ejecting portion 31 (eject opening forming members) and the second intake portion 21 (grommets in each of which a second intake opening 21a is formed) when the resistance providing device 20 is supported by a support member 32 is approximately the same as, or comparable to, the firmness of the contact between the ejecting portion 31 (eject opening forming members) and the third intake openings 83 (grommets in each of which a third intake opening 83 is formed) when the container 80 is supported by the support member 32. In the present embodiment, since each container 80 is a reticle pod configured to hold one or more reticles, the total weight of the resistance providing device 20 is set to be identical to the total weight of a container 80 that holds one reticle, for example.

By placing a resistance providing device 20, that has the structure described above, on a support member 32, the clean gas ejected from the ejecting portion 31 can be allowed to flow into the second gas lines 22 through the second intake portion 11. In the present embodiment, clean gas ejected from each of the eject openings 31a flows into a second gas line portion 22a through the second intake opening 21a to which the eject opening 31a is connected. With a resistance providing device 20a supported by a support member 32, the flow rate of clean air that flows from the ejecting portion 31 to the second gas lines 22 depends on the inflow resistance of the resistance providing device 20. Here, the inflow resistance of the resistance providing device 20 is the resistance (pressure loss) to the flow of clean gas as the clean gas is allowed to flow into the second gas lines 22 through the second intake portion 21. In the present embodiment, the second intake portion 21 (the second intake openings 21a) of the resistance providing device 20 is not provided with any valves that correspond to the intake opening and closing valves provided in the third intake openings 83 of a container 80. Therefore, the inflow resistance of the resistance providing device 20 depends mainly on the magnitude of the resistance that the second resisting member 23 provides to the flow of gas within the second gas lines 22.

As described above, in the present embodiment, the flow measuring system includes the resistance providing devices 20 in addition to the flow measuring device 10. And as with the flow measuring device 10, this resistance providing device 20 is configured such that the magnitude of inflow resistance can be adjusted. Thus, for example, no resistance providing device 20 is used in an inspection in which a container 80 (referred to, hereinafter, as "the first container") which is the target of estimation of the supply flow rate of clean gas is supported by a support member 32 (referred to, hereinafter, as "the first support member") and in which no container 80 (referred to, hereinafter, as "second container") that is not a target of estimation of the supply flow rate of clean gas is assumed to be supported by another support member 32 (another support member 32 that belongs to the same support member group and referred to hereinafter as "a second support member"). And by placing the flow measuring device 10 whose magnitude of inflow resistance is adjusted to match the inflow resistance of the first container on the first support member, it is possible to obtain the flow rate (measured with the flow meters 15 of the flow measuring device 10) that has a value close to the flow rate that is actually supplied to inside the first container under the assumed circumstance. In addition, in an inspection in which a second container is assumed to be supported by the second support member, by placing the flow measuring device 10 (whose magnitude of inflow resistance is adjusted to match the inflow resistance of the first container) on the first support member and by placing a resistance providing device 20 (whose magnitude of inflow resistance is adjusted to match the inflow resistance of the second container) on the second support member, it is possible to obtain the flow rate measured with the flow meters 15 of the flow measuring device 10 that has a value close to the flow rate that is actually supplied to inside the first container under the assumed circumstance. In addition, when each of a plurality of second support members is assumed to support a second container, a resistance providing device 20 whose magnitude of inflow resistance is adjusted to match the inflow resistance of a second container to be supported by a second support member is placed on the second support member, for each of the plurality of second support members.

As such, even if the flow rate of clean gas supplied to inside a container 80 supported by a support member 32 changes or varies depending on whether one or more containers 80 are supported by other support members 32 that belong to the same support member group and/or on the magnitudes of the inflow resistance of containers 80 supported by other support members 32 that belong to the same support member group, it is possible, by using one or more resistance providing devices 20 as necessary, to obtain a flow rate measured by the flow meters 15 of the flow measuring device 10 that has a value close to the flow rate of clean gas that is actually supplied to inside the container 80 under the assumed circumstance. As a result, it becomes possible to accurately estimate the flow rate of clean gas supplied to inside a container 80 under the assumed circumstance based on the flow rate measured by the flow meters 15. In addition, the flow measuring system may include a plurality of flow measuring devices 10. In this case, by placing the plurality of flow measuring devices 10 on mutually different support members 32 that belong to the same support member group, it becomes possible to take measurements of the flow rates of clean gas ejected from ejecting portions 31 in mutually different support members 32 simultaneously, or at approximately the same time. In addition, when the flow measuring system includes a plurality of flow measuring devices 10, some of these flow measuring devices 10 may also be used as resistance providing devices 20. In this case, measurements are not taken by the flow meters 15 in these flow measuring devices 10 that are used as resistance providing devices 20; and, they would function only as resistance providing devices 20.

Other Embodiments

Other embodiments of the flow measuring device and the flow measuring system are described next. Note that any arrangement disclosed in each of following embodiments and the embodiment described above may be used or applied in combination with any arrangement disclosed in one or more other embodiments unless such combination give rise to an inconsistency.

(1) In the embodiment described above, an example is described in which the first resisting member 13 of the flow measuring device 10 is provided to the second gas line portion 12b. However, the arrangement may be such that each of the first gas line portions 12a has a first resisting member 13 provided thereto. In this case, one or both of the first resisting members 13 may be located either upstream or downstream of the corresponding flow meter 15. In addition, in this case, the arrangement may be such that the first gas lines 12 do not include the second gas line portion 12b. In addition, in the embodiment described above, an example is described in which the second resisting member 23 of the resistance providing device 20 is provided to the fourth gas line portion 22b. However, the arrangement may be such that each of the third gas line portions 22a has a second resisting member 23 provided thereto. In this case, the arrangement may be such that the second gas lines 22 do not include the fourth gas line portion 22b.

(2) In the embodiment described above, an example is described in which each of the plurality of first gas line portions 12a has a flow meter 15 provided thereto. However, the arrangement may be such that a flow meter 15 is provided in the second gas line portion 12b. In this case, the flow meter 15 may be located upstream or downstream of the first resisting member 13.

(3) In the embodiment described above, an example is described in which the first intake portion 11 includes two first intake openings 11a whereas the first gas lines 12 include two first gas line portions 12a each of which is connected to the corresponding first intake opening 11a. However, the invention is not limited to such an arrangement. For example, the arrangement may be such that the first intake portion 11 includes three or more first intake openings 11a whereas the first gas lines 12 include three or more first gas line portions 12a each of which is connected to the corresponding first intake opening 11a. In addition, the first intake portion 11 may include a single first intake opening 11a; and, a single pipe connected to the first intake opening 11a may be provided in place of the first gas lines 12. In addition, in the embodiment described above, an example is described in which the second intake portion 21 includes two second intake openings 21a whereas the second gas lines 22 include two third gas line portions 22a each of which is connected to the corresponding second intake opening 21a. However, the invention is not limited to such an arrangement. For example, the arrangement may be such that the second intake portion 21 includes three or more second intake openings 21a whereas the second gas lines 22 include three or more third gas line portions 22a each of which is connected to the corresponding second intake opening 21a. In addition, the second intake portion 21 may include a single first intake opening 21a; and, a single pipe connected to the second intake opening 21a may be provided in place of the second gas lines 22.

(4) In the embodiment described above, an example is described in which the first resisting member 13 is a speed control valve which can adjust the flow rate of gas that flows downstream therefrom. However, the invention is not limited to such an arrangement. Instead, the first resisting member 13 may be so configured that it can be removed from the corresponding portion of the first gas lines 12. And the magnitude of the resistance provided by the first resisting member 13 may be changed by replacing the first resisting member 13 with another with a different resistance. Also, in the embodiment described above, an example is described in which the second resisting member 23 is a speed control valve which can adjust the flow rate of gas that flows downstream therefrom. However, the invention is not limited to such an arrangement. Instead, the second resisting member 23 may be so configured that it can be removed from the corresponding portion of the second gas lines 22. And the magnitude of the resistance provided by the second resisting member 23 may be changed by replacing the second resisting member 23 with another with a different resistance.

(5) In the embodiment described above, an example is described in which valves that correspond to the intake opening and closing valves provided in the third intake openings 83 of a container 80 are not provided to the first intake portion 11 (first intake openings 11a) of the flow measuring device 10, or to the second intake portion 21 (second intake openings 21a) of each resistance providing device 20. However, the invention is not limited to such an arrangement. Instead, valves that correspond to the intake opening and closing valves provided in the third intake openings 83 of a container 80 may be provided to the first intake portion 11, and/or to the second intake portion 21. In this case, the inflow resistance of the flow measuring device 10 depends mainly on the magnitude of the resistance that the first resisting member 13 provides to the flow of gas in the first gas lines 12 and on the magnitude of the pressure loss cause by the valves provided in the first intake portion 11. And the inflow resistance of a resistance providing device 20 depends mainly on the magnitude of the resistance that the second resisting member 23 provides to the flow of gas in the second gas lines 22 and on the magnitude of the pressure loss cause by the valves provided in the second intake portion 21.

(6) In the embodiment described above, an example is described in which each container 80 is a reticle pod configured to hold one or more reticles. However, the container 80 may be a FOUP (Front Opening Unified Pod) configured to hold a plurality of semiconductor wafers. In addition, objects held in any one container 80 may be any object or objects that are not reticles or semiconductor wafers, such as any industrial product, food, medicine, etc.

(7) In the embodiment described above, an example is described in which the flow measuring device and the flow measuring system are used to inspect a clean gas supplying device 30 provided to a container storage facility 100. However, the flow measuring device and the flow measuring system may be used to inspect a clean gas supplying device which is provided to a facility other than a container storage facility.

(8) Concerning any other arrangement, the embodiments disclosed in the present description should be understood to serve only as examples in all aspects. Accordingly, a person skilled in the art will be able to make various changes and modification to the disclosed arrangements without departing from the spirit of the present disclosure.

Summary of Embodiments Described Above

A brief summary of the flow measuring device and the flow measuring system described above is provided next.

A flow measuring device is used to inspect a clean gas supplying device that includes one or more support members each configured to support a container, an ejecting portion provided to each of the one or more support members and configured to eject clean gas to inside a container supported by corresponding one of the one or more support members. The flow measuring device is configured to measure a flow rate of clean gas ejected from the ejecting portion when the flow measuring device is supported by a support member. The flow measuring device comprises an intake portion configured to be connected to the ejecting portion, one or more gas lines each of which is connected to the intake portion and which is configured to allow gas ejected from the ejecting portion to flow therein, one or more flow meters each of which is configured to measure a flow rate of gas that flows through corresponding one of the one or more gas lines, at least one resisting member configured to provide resistance to flow of gas in at least one of the one or more gas lines, a main body portion which includes one or more supported portions each configured to be supported by the support member, the main body portion being configured to support the intake portion, the one or more gas lines, the one or more flow meters, and the at least one resisting member wherein a magnitude of the resistance provided by the at least one resisting member is adjustable.

By using the flow measuring device so arranged and by placing the flow measuring device on a support member so that the ejecting portion and the intake portion are connected, or in contact, with, each other, clean gas ejected from the ejecting portion can be allowed to flow into the one or more gas lines from the intake portion. The flow rate measured by the one or more flow meters under this condition depends on the inflow resistance of the flow measuring device, which is the resistance to the flow of clean gas as the clean gas is allowed to flow into the one or more gas lines through the intake portion. That is, the flow rate measured by the one or more flow meters has a value that is close to the flow rate of clean gas supplied to inside a container when the container supported by a support member has an inflow resistance that is comparable in magnitude to the inflow resistance of the flow measuring device. As a result, the flow rate of clean gas supplied to inside a container that has an inflow resistance that is comparable in magnitude to the inflow resistance of the flow measuring device can be estimated accurately based on the flow rate measured by the one or more flow meters.

And since the magnitude of the resistance provided by the at least one resisting member is adjustable in the arrangement described above, the magnitude of the inflow resistance of the flow measuring device can be changed by adjusting the magnitude of the resistance provided by the at least one resisting member. Thus, the flow rate of the clean gas supplied to inside a container can be estimated accurately not only for containers that have inflow resistance of a certain magnitude but also for containers that have inflow resistance that is within a range over which the inflow resistance of the flow measuring device can be adjusted. That is, even when there are variations in the inflow resistance among the containers, the flow rate of the clean gas supplied to inside a container can be estimated accurately for each of a plurality of containers having mutually different inflow resistance by taking measurements using one flow measuring device.

As such, with the arrangement described above, a flow measuring device can be provided with which, even when there are variations in the inflow resistance among the containers, the flow rate of the clean gas supplied to inside a container can be estimated accurately for each of a plurality of containers having mutually different inflow resistance.

Here, the ejecting portion preferably includes a plurality of eject openings, wherein the intake portion preferably includes a plurality of intake openings each of which is configured to be connected to corresponding one of the plurality of eject openings, wherein the one or more gas lines preferably include a plurality of first gas line portions each of which is connected to corresponding one of the plurality of intake openings, wherein the at least one resisting member is preferably provided to provide resistance to a flow of gas in each of the plurality of first gas line portions, and wherein each of the plurality of first gas line portions preferably has corresponding one of the one or more flow meters provided thereto.

With the arrangement described above, since data for the flow rate of clean gas for each eject opening can be obtained based on an inspection using the flow measuring device, it is possible to learn the presence, and degree, of any variations in the clean gas ejection rates among the plurality of eject openings, in addition to the estimated flow rate of clean gas supplied to inside a container. Therefore, it is possible to obtain more information about the state of the clean gas supplying device by inspecting the clean gas supplying device using the flow measuring device.

In addition, the ejecting portion preferably includes a plurality of eject openings, wherein the intake portion preferably includes a plurality of intake openings each of which is configured to be connected to corresponding one of the plurality of eject openings, wherein the one or more gas lines preferably include a plurality of first gas line portions each of which is connected to corresponding one of the plurality of intake openings, and a second gas line portion which is connected to an end portion, on an opposite side from a corresponding intake opening, of each of the plurality of first gas line portions, and in which the gas that is a combination of gas that flows through all of the plurality of first gas line portions flows, wherein the at least one resisting member is preferably a single resisting member provided to the second gas line portion.

With the arrangement described above, the resistance (resistance to the gas that flows through inside) of a plurality of first gas line portions can be adjusted by adjusting the resisting member provided to the second gas line portion. Thus, adjusting the inflow resistance of the flow measuring device can be simplified compared with an arrangement in which each of the first gas line portions is provided with its own resisting member. In addition, compared with an arrangement in which each of the first gas line portions is provided with its own resisting member, the above arrangement offers an additional advantage of facilitating reduction in any variations in the magnitude of resistance to the internal gas flow, among the plurality of first gas lines.

A flow measuring system is used to inspect a clean gas supplying device that includes a plurality of support members each configured to support a container, an ejecting portion provided to each of the plurality of support members and configured to eject clean gas to inside a container supported by corresponding one of the plurality of support members, a primary gas line to which clean gas is supplied from a supply source of clean gas, a flow control device configured to control a flow rate of clean gas that flows through the primary gas line, and a plurality of branch gas lines, each of which branches off from the primary gas line at a location downstream of the flow control device, and each of which is connected to a corresponding ejecting portion. The flow measuring system comprises: the flow measuring device; one or more resistance providing devices each of which is capable of being supported by one of the plurality of support members that is different from the support member on which the flow measuring device is supported, wherein, with a first intake portion being the intake portion, one or more first gas lines being the one or more gas lines, a first resisting member being the resisting member, a first main body portion being the main body portion, one or more first supported portions being the one or more supported portions, each of the one or more resistance providing devices includes: a second intake portion configured to be connected to the ejecting portion; one or more second gas lines each of which is connected to the second intake portion and in which gas ejected from the ejecting portion flows; at least one second resisting member configured to provide resistance to flow of gas in at least one of the one or more second gas lines; and a second main body portion which includes one or more second supported portions each configured to be supported by a support member, the second main body portion being configured to support the second intake portion, the one or more second gas lines, and the at least one second resisting member, wherein a magnitude of the resistance provided by each of the at least one second resisting member is adjustable.

With the clean gas supplying device so arranged, the flow rate of clean gas ejected from one ejecting portion can easily be affected by the effect of the flow rate of clean gas ejected from other ejecting portions, compared with an arrangement in which a flow control device is provided to each of the plurality of branch gas lines. As a result, the flow rate of clean gas supplied to inside a container supported by a support member 32 may change depending not only on the magnitude of the inflow resistance of that container but also on whether any containers are supported by other support members, and on the magnitudes of the inflow resistance of the containers supported by other support members.

With the arrangement described above, the flow measuring system is provided with one or more resistance providing devices in addition to the flow measuring device. And each of the one or more resistance providing devices is configured such that as with the flow measuring device, the magnitude of its inflow resistance (resistance to the flow of clean gas as the clean gas is allowed to flow into the second gas lines through the second intake portion) can be adjusted. Thus, for example, no resistance providing device is used in an inspection in which a container (referred to, hereinafter, as "the first container") which is the target of estimation of the supply flow rate of clean gas is supported by a support member (referred to, hereinafter, as "the first support member") and in which no container (referred to, hereinafter, as "second container") that is not a target of estimation of the supply flow rate of clean gas is assumed to be supported by another support member (referred to hereinafter as "a second support member"). And by placing the flow measuring device whose magnitude of inflow resistance is adjusted to match the inflow resistance of the first container on the first support member, it is possible to obtain the flow rate (measured with the one or more flow meters of the flow measuring device) that has a value close to the flow rate that is actually supplied to inside the first container under the assumed circumstance. In addition, in an inspection in which a second container is assumed to be supported by the second support member, by placing the flow measuring device (whose magnitude of inflow resistance is adjusted to match the inflow resistance of the first container) on the first support member and by placing a resistance providing device (whose magnitude of inflow resistance is adjusted to match the inflow resistance of the second container) on the second support member, it is possible to obtain the flow rate measured with the one or more flow meters of the flow measuring device that has a value close to the flow rate that is actually supplied to inside the first container under the assumed circumstance. As such, even if the flow rate of clean gas supplied to inside a container supported by a support member changes depending on whether one or more containers are supported by other support members and/or on the magnitudes of the inflow resistance of other containers supported by other support members, it is possible, by using one or more resistance providing devices as necessary, to obtain a flow rate measured by the one or more flow meters of the flow measuring device that has a value close to the flow rate of clean gas that is actually supplied to inside the container under the assumed circumstance. As a result, it becomes possible to accurately estimate the flow rate of clean gas supplied to inside a container under the assumed circumstance based on the flow rate measured by the one or more flow meters.

What is claimed is:

1. A flow measuring device that is used to inspect a clean gas supplying device that includes one or more support members each configured to support a container, an ejecting portion provided to each of the one or more support members and configured to eject clean gas to inside a container supported by corresponding one of the one or more support members, the flow measuring device being configured to measure a flow rate of clean gas ejected from the ejecting portion when the flow measuring device is supported by a support member, the flow measuring device comprising:
an intake portion configured to be connected to the ejecting portion;
one or more gas lines each of which is connected to the intake portion and which is configured to allow gas ejected from the ejecting portion to flow therein;
one or more flow meters each of which is configured to measure a flow rate of gas that flows through corresponding one of the one or more gas lines;
at least one resisting member configured to provide resistance to flow of gas in at least one of the one or more gas lines;
a main body portion which includes one or more supported portions each configured to be supported by the support member, the main body portion being configured to support the intake portion, the one or more gas lines, the one or more flow meters, and the at least one resisting member; and
wherein a magnitude of the resistance provided by the at least one resisting member is adjustable.

2. The flow measuring device as defined in claim 1, wherein the ejecting portion includes a plurality of eject openings,
wherein the intake portion includes a plurality of intake openings each of which is configured to be connected to corresponding one of the plurality of eject openings,
wherein the one or more gas lines include a plurality of first gas line portions each of which is connected to corresponding one of the plurality of intake openings,
wherein the at least one resisting member is provided to provide resistance to a flow of gas in each of the plurality of first gas line portions, and
wherein each of the plurality of first gas line portions has corresponding one of the one or more flow meters provided thereto.

3. The flow measuring device as defined in claim 1, wherein the ejecting portion includes a plurality of eject openings,
wherein the intake portion includes a plurality of intake openings each of which is configured to be connected to corresponding one of the plurality of eject openings,
wherein the one or more gas lines include a plurality of first gas line portions each of which is connected to corresponding one of the plurality of intake openings, and a second gas line portion which is connected to an end portion, on an opposite side from a corresponding intake opening, of each of the plurality of first gas line portions, and in which the gas that is a combination of gas that flows through all of the plurality of first gas line portions flows,
wherein the at least one resisting member is a single resisting member provided to the second gas line portion.

4. A flow measuring system that is used to inspect a clean gas supplying device that includes a plurality of support members each configured to support a container, an ejecting portion provided to each of the plurality of support members and configured to eject clean gas to inside a container supported by corresponding one of the plurality of support members, a primary gas line to which clean gas is supplied from a supply source of clean gas, a flow control device configured to control a flow rate of clean gas that flows through the primary gas line, and a plurality of branch gas lines, each of which branches off from the primary gas line at a location downstream of the flow control device, and each of which is connected to a corresponding ejecting portion, the flow measuring system comprising:
the flow measuring device as defined in claim 1;
one or more resistance providing devices each of which is capable of being supported by one of the plurality of support members that is different from the support member on which the flow measuring device is supported;
wherein, with a first intake portion being the intake portion, one or more first gas lines being the one or more gas lines, a first resisting member being the resisting member, a first main body portion being the main body portion, one or more first supported portions being the one or more supported portions,
each of the one or more resistance providing devices includes: a second intake portion configured to be connected to the ejecting portion; one or more second gas lines each of which is connected to the second intake portion and in which gas ejected from the ejecting portion flows; at least one second resisting member configured to provide resistance to flow of gas in at least one of the one or more second gas lines; and a second main body portion which includes one or more second supported portions each configured to be supported by a support member, the second main body portion being configured to support the second intake portion, the one or more second gas lines, and the at least one second resisting member, and wherein a magnitude of the resistance provided by each of the at least one second resisting member is adjustable.

\* \* \* \* \*

UNITED STATES PATENT AND TRADEMARK OFFICE
CERTIFICATE OF CORRECTION

PATENT NO. : 10,006,894 B2  
APPLICATION NO. : 15/699018  
DATED : June 26, 2018  
INVENTOR(S) : Takeshi Abe et al.

Page 1 of 1

It is certified that error appears in the above-identified patent and that said Letters Patent is hereby corrected as shown below:

On the Title Page

Column 1, Line 3, after "0 days." delete "days."

Signed and Sealed this  
Twenty-fifth Day of September, 2018

Andrei Iancu  
*Director of the United States Patent and Trademark Office*